United States Patent

Heckmann et al.

[11] Patent Number: 5,986,103
[45] Date of Patent: Nov. 16, 1999

[54] 2-ALKYL-1H-IMIDAZOLE-5-CARBOXYLIC ACIDS

[75] Inventors: Bertrand Heckmann, Cachan; Simone Jouquey, Paris; Jean-Paul Vevert, Pantin; Jidong Zhang, Paris, all of France

[73] Assignee: Hoechst Marion Roussel, France

[21] Appl. No.: 09/068,615

[22] PCT Filed: Nov. 7, 1996

[86] PCT No.: PCT/FR96/01750

§ 371 Date: Jun. 9, 1998

§ 102(e) Date: Jun. 9, 1998

[87] PCT Pub. No.: WO97/17340

PCT Pub. Date: May 15, 1997

[30] Foreign Application Priority Data

Aug. 11, 1995 [FR] France .................................. 95 13190

[51] Int. Cl.⁶ ...................... C07D 405/06; A61K 31/415; A61K 31/36
[52] U.S. Cl. ........................ 548/311.7; 514/396; 514/397
[58] Field of Search .................... 548/311.7; 514/396, 514/397

[56] References Cited

FOREIGN PATENT DOCUMENTS 9414434  7/1994  WIPO .
9604276  2/1996  WIPO .

*Primary Examiner*—Floyd D. Higel
*Attorney, Agent, or Firm*—Bierman, Muserlian and Lucas

[57] ABSTRACT

The invention relates to the new products of formula (I):

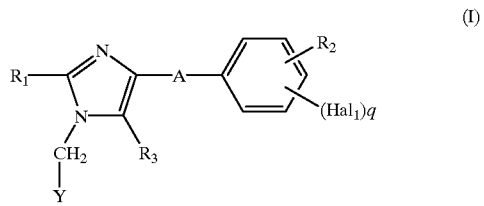

in which:
- $R_1$ represents alkyl,
- A represents a sulphur or oxygen atom,
- $R_2$ represents carboxy, tetrazolyl or alkyl, alkoxy, alkylthio substituted by a carboxy or a tetrazolyl,
- $Hal_1$ is halogen, q represents an integer from 0 to 4,
- $R_3$ is formyl, carboxy or tetrazolyl,
- Y represents phenyl substituted by a dioxol radical and optionally by a halogen atom, or by an alkyl or alkoxy radical as well as all the possible racemic, enantiomeric and diastereoisomeric isomer forms, as well as the addition salts of said products of formula (I).

5 Claims, No Drawings

2-ALKYL-1H-IMIDAZOLE-5-CARBOXYLIC ACIDS

This application is a 371 of PCT/FR96,01750 filed Nov. 7, 1996.

The present invention relates to new imidazole derivatives, their preparation process, the new intermediates obtained, their use as medicaments, the pharmaceutical compositions containing them and the new use of imidazole derivatives.

A subject of the present invention is the products of formula (I):

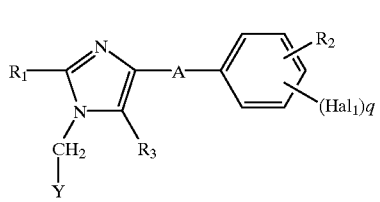

in which:

R$_1$ represents a linear or branched alkyl radical containing 2 to 6 carbon atoms, A represents a sulphur or oxygen atom, R$_2$ represents a free, salified or esterified carboxy radical or a free or salified tetrazolyl radical, or a linear or branched alkyl, alkoxy or alkylthio radical containing at most 4 carbon atoms and substituted by a free, salified or esterified carboxy radical or by a free or salified tetrazolyl radical, Hal$_1$ represents a halogen atom and q represents an integer From 0 to 4, R$_3$ represents a formyl radical, a free, salified or esterified carboxy radical, or a free or salified tetrazolyl radical, Y represents a phenyl radical substituted by a dioxol radical and optionally by a halogen atom, or by an alkyl or alkoxy radical containing at most 4 carbon atoms, said products of formula (I) being in all the possible racemic, enantiomeric and diastereoisomeric isomer forts, as well as the addition salts with mineral and organic acids or with mineral and organic bases of said products of formula (I).

In the products of formula (I) and in what follows:

the term linear or branched alkyl radical designates the following radicals: methyl, ethyl, propyl, isopropyl, butyl, isobutyl, sec-butyl, tert-butyl, pentyl, isopentyl, hexyl, isohexyl and also heptyl, octyl, nonyl and decyl as well as their linear or branched position isomers, the term linear or branched alkoxy radical designates the following radicals: methoxy, ethoxy, propoxy, isopropoxy, linear, secondary or tertiary butoxy, pentoxy or hexoxy as well as their linear or branched position isomers, the term halogen atom preferably designates the chlorine atom, but can also represent a fluorine, bromine or iodine atom, Hal$_1$ preferably represents a fluorine atom.

The carboxy radical or radicals of the products of formula (I) can be salified or esterified by various groups known to a man skilled in the art amongst which there can be mentioned, for example:

among the salification compounds, mineral bases such as, for example, an equivalent of sodium, potassium, lithium, calcium, magnesium or ammonium or organic bases such as, for example, methylamine, propylamine, trimethylamine, diethylamine, triethylamine, N,N-dimethylethanolamine, tris (hydroxymethyl) amino methane, ethanolamine, pyridine, picoline, dicyclohexylamine, morpholine, benzylamine, procaine, lysine, arginine, histidine, N-methylglucamine, among the esterification compounds, the alkyl radicals in order to form alkoxy carbonyl groups such as, for example, methoxycarbonyl, ethoxycarbonyl, tert-butoxycarbonyl or benzyloxycarbonyl, these alkyl radicals being able to be substituted by radicals chosen for example from halogen atoms, the following radicals: hydroxyl, alkoxy, acyl, acyloxy, alkylthio, amino or aryl such as, for example, in the following groups: chloromethyl, hydroxypropyl, methoxymethyl, propionyloxymethyl, methylthiomethyl, dimethylaminoethyl, benzyl or phenethyl.

The addition salts with mineral or organic acids of the products of formula (I) can be, for example, the salts formed with the following acids: hydrochloric, hydrobromic, hydroiodic, nitric, sulphuric, phosphoric, propionic, acetic, formic, benzoic, maleic, fumaric, succinic, tartaric, citric, oxalic, glyoxylic, aspartic, ascorbic, alkylmonosulphonic such as for example methanesulphonic, ethanesulphonic, propanesulphonic, alkyldisulphonic such as for example methanedisulphonic, alpha, beta-ethanedisulphonic, aryl-monosulphonic such as benzenesulphonic and aryldisul-phonic.

Therefore a subject of the present invention is the products of formula (I) as defined above in which:

R$_1$ represents an ethyl, n-propyl, isopropyl, n-butyl, isobutyl or terbutyl radical, A represents a sulphur atom, R$_2$ represents a linear or branched alkyl or alkoxy radical containing at most 4 carbon atoms and substituted by a free, salified or esterified carboxy radical, q is equal to 0, R$_3$ represents a free, salified or esterified carboxy radical, or a free or salified tetrazolyl radical, Y represents a phenyl radical substituted by a dioxol radical and optionally by a halogen atom, said products of formula (I) being in all the possible racemic, enantiomeric and diastereoisomeric isomer forms, as well as the addition salts with mineral and organic acids or with mineral and organic bases of said products of formula (I).

A particular subject of the present invention is the following products:

4-((4-(carboxymethoxy)phenyl)thio)-1-((6-chloro-1,3-benzodioxol-5-yl)methyl)-2-propyl-1H-imidazole-5-carboxylic acid, 4-((4-(2-carboxyethyl)phenyl)thio)-1-((6-chloro-1,3-benzodioxol-5-yl)methyl)-2-(1-methylethyl)-1H-imidazole-5-carboxylic acid, 4-((4-carboxyphenyl)thio) 1-((6-chloro 1,3-benzodioxol-5-yl)methyl) 2-propyl 1H-imidazole 5-carboxylic acid.

In the products of formula (I) and in what follows:

the term alkylthio radical designates the radicals in which the alkyl radical is as defined above such as for example in methylthio, ethylthio, propylthio, isopropylthio, butylthio, sec-butylthio, tert-butylthio, isopentylthio, isohexylthio, but also heptylthio, octylthio, nonylthio or decylthio as well as their linear or branched position isomers.

A subject of the present invention is also the preparation process for the products of formula (I), as defined above, characterized in that:

either a compound of formula (II):

(II)

$$R'_1 \underset{H}{\overset{N}{\underset{N}{\bigvee}}} H$$

in which $R'_1$ has the meaning indicated above for $R_1$, in which the optional reactive functions are optionally protected by protective groups, is subjected to a reaction with a compound of formula (III):

(III)

$$\underset{Y'}{\overset{Hal}{\diagup}}$$

in which Hal represents a halogen atom, and Y' has the meaning indicated above for Y, in which the optional reactive functions are optionally protected by protective groups, in order to obtain the product of formula (IV):

(IV)

$$R'_1 \underset{\underset{Y'}{\bigvee}}{\overset{N}{\underset{N}{\bigvee}}} H$$

in which $R'_1$ and Y' have the meanings indicated above, which product of formula (IV) can be subjected to a halogenation reaction, in order to obtain the product of formula (V):

(V)

$$R'_1 \underset{\underset{Y'}{\bigvee}}{\overset{N}{\underset{N}{\bigvee}}} Hal$$

in which $R'_1$, Hal and Y' have the meanings indicated above, or a compound of formula (VI):

(VI)

$$Hal \underset{H}{\overset{N}{\underset{N}{\bigvee}}} Hal$$

in which Hal has the meaning indicated above, is subjected either to a reaction with the compound of formula (III) as defined above, or to the action of a protective group P, in order to obtain a product of formula (VII):

(VII)

$$Hal \underset{W}{\overset{N}{\underset{N}{\bigvee}}} Hal$$

in which Hal has the meaning indicated above and W represents represents a protective group of the nitrogen atom, which product of formula (VII) is subjected to a halogen-metal exchange reaction then to a reaction with dimethylformamide or with an electrophile of formula (VIIIa) or (VIIIb):

$$L_1\text{—}CHO \quad (VIII_a)$$

$$L_1\text{—}CO\text{—}Cl \quad (VIII_b)$$

in which $L_1$ represents a linear or branched alkyl radical containing at most 6 carbon atoms and optionally substituted by a protected alkoxy or hydroxyl radical, in order to obtain a product of formula (IX):

(IX)

$$R''_1 \underset{W}{\overset{N}{\underset{N}{\bigvee}}} Hal$$

in which Hal and W have the meanings indicated above, $R''_1$ represents an alkyl-carbonyl, formyl or hydroxyalkyl radical in which the alkyl radical has the meaning indicated above and in which the optional reactive functions are optionally protected by protective groups, which products of formulae (V) and (IX) can be subjected to a halogen-metal exchange reaction on one of the halogen atoms then to a reaction with $CO_2$ or dimethylformamide or an electrophilic compound of formula (X):

(X)

$$Cl\text{—}\underset{\underset{O}{\|}}{C}\text{-Oalk}$$

in which alk represents an alkyl radical containing at most 4 carbon atoms, in order to obtain the compound of formula (XI):

(XI)

$$R'''_1 \underset{W}{\overset{N}{\underset{N}{\bigvee}}} Hal$$

in which $R'''_1$ represents $R'_1$ or $R''_1$ as defined above, Hal, Y' and W have the meanings indicated above and $Z_3$ represents the free or esterified carboxy radical or the formyl radical, which compound of formula (XI) can be subjected to a reaction with a compound of formula (XII):

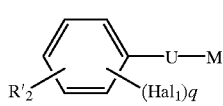
(XII)

in which U represents a sulphur or oxygen atom, M represents a metal such as sodium, potassium or copper, $Hal_1$ and q have the meaning indicated above, $R'_2$ represents $R_2$ as defined above, in which the optional reactive functions are optionally protected by protective groups in order to obtain the compound of formula (XIII):

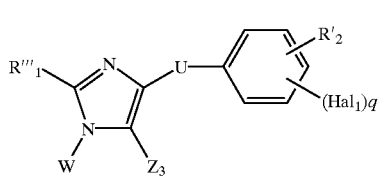
(XIII)

in which $R'''_1$, U, $R'_2$ $Hal_1$, q and W have the meanings indicated above, which product of formula (XIII), when $Z_3$ represents the formyl radical, can be subjected to an oxidation reaction in order to obtain the product of formula (XIV):

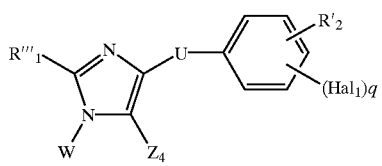
(XIV)

in which $R'''_1$, U, $R'_2$, $Hal_1$, q and W have the meanings indicated above, and $Z_4$ represents the cyano radical or the carboxy radical free or esterified by a linear or branched alkyl radical containing at most 6 carbon atoms, which products of formula (XIII) or (XIV), in the case where W represents P as defined above and after release of the amine function blocked by P as defined above, are reacted with the compound of formula (III) as defined above, in order to obtain a product of formula (XV):

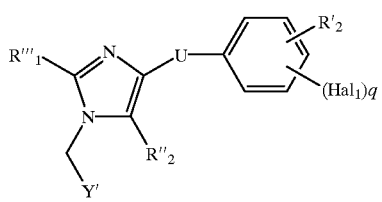
(XV)

in which $R'''_1$, U, $R'_2$, $Hal_1$, q and Y' have the meanings indicated above, and $R''_3$ represents $Z_3$ or $Z_4$ as defined above, or a compound of formula (XX):

Y'—CHO
(XX)

in which Y' has the meaning indicated above, is subjected to a compound of formula (XXI):

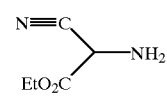
(XXI)

in order to obtain a product of formula (XXII):

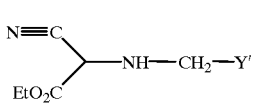
(XXII)

in which Y' has the meaning indicated above, which is subjected to a compound of formula (XXIII):

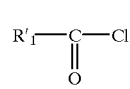
(XXIII)

in which $R'_1$ has the meaning indicated above, in order to obtain the product of formula (XXIV):

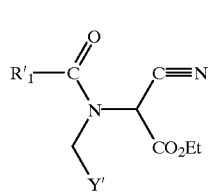
(XXIV)

in which Y' and $R'_1$ have the meanings indicated above, which is subjected to a compound of formula (XXV):

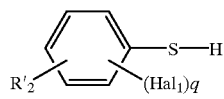
(XXV)

in which $R'_2$, $Hal_1$ and q have the meaning indicated above, in order to obtain the product of formula (XXVI):

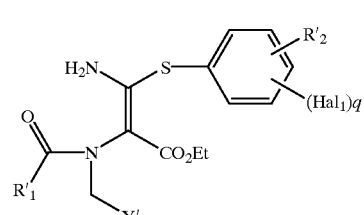
(XXVI)

in which Y', R'$_1$, R'$_2$, Hal$_1$ and q have the meanings indicated above, which is cyclized into the product of formula (I$_2$):

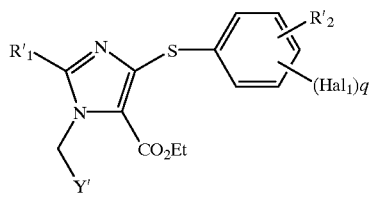

(I$_2$)

in which Y', R'$_1$, R'$_2$, Hal$_1$ and q have the meanings indicated above, which products of formulae (IX), (XI), (XIII), (XIV), (XV) and (I$_2$) can be products of formula (I) and which, in order to obtain products or other products of formula (I), can be subjected, if desired and if necessary, to one or more of the following conversion reactions, in any order:

a) an esterification reaction of the acid function, b) a saponification reaction of the ester function into an acid function, c) a conversion reaction of the free or esterified carboxy function into a formyl radical, d) a conversion reaction of the cyano function into an acid function, e) an oxidation reaction of the alkylthio group into a corresponding sulphoxide or sulphone, f) a reduction reaction of the free or esterified carboxy function into an alcohol function, g) a conversion reaction of the alkoxy function into a hydroxyl function, or also of the hydroxyl function i:to an alkoxy function, h) an oxidation reaction of the alcohol function into an aldehyde, acid or ketone function, i) a conversion reaction of the formyl radical into a carbamoyl radical, j) a conversion reaction of the carbamoyl radical into a nitrile radical, k) a conversion reaction of the nitrile radical into tetrazolyl, l) a conversion reaction of a halogenated function into a formyl or esterified carboxy function, m) a conversion reaction of a formyl radical into a CH$_2$—CO$_2$alk or CH=CH—CO$_2$alk function in which alk represents an alkyl radical containing 1 to 4 carbon atoms, then if appropriate, conversion into a corresponding acid, n) a conversion reaction of a formyl radical into a

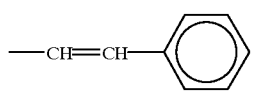

radical then if appropriate into a

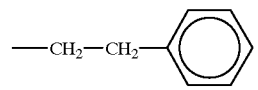

radical,

o) an oxidation reaction of the S-alk radical into S-alk then conversion into an SH function and if appropriate into S-A' in which alk and A' have the meaning indicated previously, p) an elimination reaction of the protective groups which can be carried by the protected reactive functions, q) a salification reaction by a mineral or organic acid or by a base in order to obtain the corresponding salt, r) a resolution reaction of the racemic forms into resolved products, said products of formula (I) thus obtained being in all the possible racemic, enantiomeric and diastereoisomeric isomer forms.

It can be noted that such conversion reactions of substituents into other substituents can also be carried out on the starting products as well as on the intermediate products as defined above before continuing with the synthesis according to the reactions indicated in the process described above.

Under preferential conditions for implementing the invention, the process described above can be carried out in the following manner. In the product of formula (III), the halogen atom preferably represents a bromine atom but can also represent a chlorine or iodine atom. The condensation reaction of the imidazoles of the formulae as defined above (II), (VI), (XVI), (XIII) and (XIV) (in the case of the products of formulae (XIII) and (XIV), when W represents P and after deprotection of the nitrogen atom), with the compound of formula (III) as defined above, in order to obtain respectively the products of formulae (IV), (VII) when W represents Y', (XV) and (I$_1$) as defined above can be carried out in a solvent such as for example dimethylformamide or also dimethylacetamide, tetrahydrofuran, dimethoxyethane or dimethylsulphoxide under reflux of the solvent or at ambient temperature, preferably under agitation; the reaction is preferably carried out in the presence of a base such as for example sodium or potassium hydride or also sodium or potassium carbonate, sodium or potassium methylate or ethylate or tert-butylate.

The halogenation reaction of the compound of formula (IV) as defined above into a compound of formula (V) as defined above, can be carried out under the usual conditions known to a man skilled in the art and in particular by bromination using NBS in CH$_2$Cl$_2$ or also Br$_2$ in acetic acid.

The compounds of formulae (V), (VII) and (IX) as defined above can be subjected to a halogen-metal exchange reaction on the halogen atom by reaction with an organometallic compound such as nBuli or ethyl magnesium bromide in a solvent such as tetrahydrofuran at a temperature of about −78° C. for Buli and at ambient temperature for ethyl magnesium bromide.

The carboxylation reaction using CO$_2$ and the formylation reaction using dimethylformamide of the compounds of formula (V) or (IX) into a compound of formula (XI) can be carried out according to the usual conditions known to a man skilled in the art, i.e. for example in tetrahydrofuran at ambient temperature.

$L_1$ represents an alkyl radical such that $R_{1''}$ represents the corresponding values chosen from the values of $R_1$ as defined above in which the optional reactive functions are optionally protected by protective groups.

The reaction of the compound of formula (V) or (IX) as defined above with the compound of formula (X), as defined above, in order to obtain the corresponding compound of formula (XI) as defined above, can be carried out in an identical manner using ethyl magnesium bromide as metallation agent in tetrahydrofuran at ambient temperature.

The reaction of the compound of formula (VII) with the compounds of formulae (VIIIa) or (VIIIb) can be carried out according to the usual conditions known to a man skilled in the art i.e. for example in tetrahydrofuran at ambient temperature.

The amine function of the compounds of formulae (XIII) and (XIV) as defined above, protected by P as defined above, can be released under the usual conditions known to a a man skilled in the art and in particular when P represents the —$CH_2$—O—$(CH_2)_2$—$Si(CH_3)_3$ radical, the hydrogen atom can be released in TFA or also in the presence of a fluoride ion.

The saponification reaction can be carried out according to the usual methods known to a man skilled in the art, such as for example in a solvent such as methanol or ethanol, dioxane or dimethoxyethane, in the presence of soda or potash or also caesium carbonate.

The reduction or oxidation reactions of the product of formula (XIII) into the product of formula (XIV) can be carried out according to the usual methods known to a man skilled in the art.

In the reactions described above, the operation can be carried out in the following manner:

the reaction of the compound of formula (XX) with the compound of formula (XXI) in order to obtain the compound of formula (XXII) can be carried out in a solvent such as for example methylene chloride in the presence of an acid. catalyst such as for example amberlist then by reduction for example using sodium borohydride in acetic acid and methylene chloride, the reaction of the compound of formula (XXII) with the compound of formula (XXIII) in order to obtain the compound of formula (XXIV) can be carried out in a solvent such as for example tetrahydrofuran or methylene chloride, in the presence of a base such as pyridine or also triethylanine or sodium or potassium carbonate, the reaction of the compound of formula (XXIV) with the compound of formula (XXV) in order to obtain the compound of formula (XXVI) can be carried out in an alcohol such as methanol or ethanol in the presence of a base such as triethylamine or pyridine.

the cyclization of the compound of formula (XXVI) into the product of formula ($I_2$) can be carried out in the presence of an anhydride such as for example propane phosphoric anhydride in ethyl acetate.

According to the values of $R'_1, R''_1, R'''_1, R'_2, R'_3, R''_3$, the products of formulae (IX), (XI), (XIII), (XIV), (XV) and ($I_2$) constitute or do not constitute products of formula (I) and can give products of formula (I), or be converted into other products of formula (I) by being subjected to one or more of the reactions a) to r) indicated above.

Thus the various reactive functions which can be carried by certain compounds of the reactions defined above can, if necessary, be protected: they are for example the hydroxyl, acyl, free carboxy or also amino and monoalkylamino radicals which can be protected by the appropriate protective groups.

The following non-exhaustive list of examples of the protection of the reactive functions can be mentioned:

the hydroxyl groups can be protected for example by alkyl radicals such as tert-butyl, trimethylsilyl, tert-butyldimethylsilyl, methoxymethyl, tetrahydropyrannyl, benzyl or acetyl, the amino groups can be protected for example by the acetyl, trityl, benzyl, tert-butoxycarbonyl, phthalimido radicals or other radicals known in the chemistry of the peptides, the acyl groups such as the formyl group can be protected for example in the form of cyclic or non-cyclic ketals or thioketals such as dimethyl or diethylketal or ethylene dioxyketal, or diethylthioketal or ethylenedithioketal, the acid functions of he products described above can be, if desired, amidified by a primary or secondary amine for example in methylene chloride in the presence, for example, of 1-ethyl-3-(dimethylaminopropyl) carbodiimide hydrochloride at ambient temperature:

the acid functions can be protected for example in the form of esters formed with easily-cleavable esters such as benzyl or terbutyl esters or esters known in the chemistry of the peptides.

The reactions to which the products of formulae (IX), (XI), (XIII), (XIV), (XV) and ($I_2$) as defined above can be subjected, if desired or if necessary, can be carried out, for example, as indicated hereafter.

a) The products described above can, if desired, be subjected, on the optional carboxy functions, to esterification reactions which can be carried out according to the usual methods known to a man skilled in the art.

b) The optional conversions of ester functions into an acid function of the products described above can, if desired, be carried out under the usual conditions known to a man skilled in the art, in particular by acid or alkaline hydrolysis for example using soda or potash in an alcoholic medium such as, for example, in methanol or also using hydrochloric or sulphuric acid.

c) The conversion reaction of the ester function

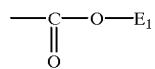

in which $E_1$ can represent an optionally substituted and optionally protected alkyl radical, into a formyl function can be carried out as described in the experimental part, or according to the usual methods known to a man skilled in the art, in particular by saponification of the ester into an acid, then converted into an acid chloride for example by the action of thionyl chloride, then reduction for example by hydrogenation on palladium.

d) The optional cyano functions of the products described above can be, if desired, converted into an acid function under the usual conditions known to a man skilled in the art for example by a double hydrolysis carried out in an acid medium such as for example in a sulphuric acid, glacial acetic acid and water mixture, these three compounds preferably being in equal proportions, or also in a mixture of soda, ethanol and water under reflux.

e) The optional alkylthio groups of the products described above can be, if desired, converted into the corresponding sulphoxide or sulphone functions under the usual conditions known to a man skilled in the art such as for example using peracids such as for example peracetic acid or metachloroperbenzoic acid or also using ozone, oxone, sodium periodate in a solvent such as for example methylene chloride or dioxane at ambient temperature.

The obtaining of the sulphoxide function can be encouraged by an equimolar mixture of the product containing an alkylthio group and the reagent such as in particular a peracid.

The obtaining of the sulphone function can be encouraged by a mixture of the product containing an alkylthio group with an excess of the reagent such as in particular a peracid.

f) The optional free or esterified carboxy functions of the products described above can be, if desired, reduced into an alcohol function by methods known to a man skilled in the art: the optional esterified carboxy functions can be, if desired, reduced into an alcohol function by methods known to a man skilled in the art and in particular by lithium and aluminium hydride in a solvent such as for example tetrahydrofuran or also dioxane or ethyl ether.

The optional free carboxy functions of the products described above can be, if desired, reduced into an alcohol function in particular by boron hydride.

g) The optional alkoxy functions such as in particular methoxy of the products described above can be, if desired, converted into a hydroxyl function under the usual conditions known to a man skilled in the art for example by boron tribromide in a solvent such as for example methylene chloride, by pyridine hydrobromide or hydrochloride or also by hydrobromic or hydrochloric acid in water or trifluoroacetic acid under reflux.

h) The optional alcohol functions of the products described above can be, if desired, converted into an aldehyde or acid function by oxidation under the usual conditions known to a man skilled in the art such as for example by the action of manganese oxide in order to obtain the aldehydes or of Jones reagent in order to obtain the acids.

i) j) The conversion reactions of the formyl radical into the carbamoyl radical and of the carbamoyl radical into the nitrile radical are carried out in particular for $R_3$ and $R_4$ according to the usual conditions known to a man skilled in the art, such as for example passage via the keto nitrile and displacement by an amine (Chem. Comm. 1971, p. 733).

k) The optional nitrile functions of the products described above can be, if desired, converted into tetrazolyl under the usual conditions known to a man skilled in the art such as for example by the cycloaddition of a metallic azide such as for example sodium azide or a trialkyltin azide on the nitrile function as indicated in the method described in the article referenced as follows:

J. Organometallic Chemistry., 33, 337 (1971) KOZIMA S. et al.

It can be noted that the conversion reaction of a carbamate into urea and in particular of a sulphonylcarbamate into sulphonylurea, can be carried out for example under reflux of a solvent such as for example toluene in the presence of a suitable amine.

l) The conversion of a halogenated radical into a formyl radical can in particular be carried out by the action of an organometallic derivative, for example ethyl magnesium bromide, in an organic solvent.

m) The conversion of the formyl radical into a CH=CH—CO₂alk radical can be carried out by a Wittig type reaction by condensation of a suitable phosphonium salt in the presence of sodium hydride; the conversion into an acid is carried out by hydrolysis, for example using a base such as soda in an alcoholic medium.

n) The conversion of the formyl radical into a

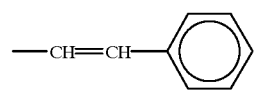

radical can be carried out by a Wittig reaction as indicated above; the conversion into a

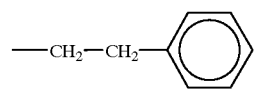

radical is carried out by reduction, using hydrogen in the presence of a catalyst, for example platinum oxide.

It can be noted that the conversion of the formyl radical into the CH₂OH radical can be carried out using a reducing agent, for example sodium borohydride in ethanol at ambient temperature; the conversion into a —CH₂—SR radical can be carried out by the action of the appropriate R—SH thiol on the intermediate mesylate prepared beforehand by the action of mesyl chloride on the alcohol in the presence of Hunig base.

o) The oxidation of the S-alk substituent into sulphoxide can be carried out for example, by the action of metachloroperbenzoic acid; the conversion of the thiol is obtained by PUMMERER's reaction for example in the presence of trifluoroacetic anhydride; the conversion of the SH substituent into SZ₂ can be obtained by the action of a halogenated derivative Hal—Z₂ for example iodocyclohexane.

It is understood that the reactions described above can be carried out according to the usual methods known to a man skilled in the art.

p) The elimination of the protective groups such as for example those indicated above can be carried out under the usual conditions known to a man skilled in the art, in particular by an acid hydrolysis carried out with an acid such as hydrochloric, benzenesulphonic or paratoluene sulphonic acid, formic or trifluoroacetic acid or also by a catalytic hydrogenation.

The phthalimido group can be eliminated by hydrazine.

A list of various protective groups which can be used will be found for example in the Patent BF 2,499,995.

q) The products described above can, if desired, be subjected to salification reactions for example using a mineral or organic acid or a mineral or organic base according to the usual methods known to a man skilled in the art.

r) The optional optically-active forms of the products described above can be prepared by resolution of the racemics according to the usual methods known to a man skilled in the art.

Illustrations of such reactions defined above are given in the preparation of the examples described hereafter.

The compounds of formula (I) as defined above as well as their addition salts with acids have useful pharmacological properties.

The products of formula (I) as defined above are endowed with antagonistic properties for the endothelin receptors and are thus in particular inhibitors of the effects of endothelin, notably the vasoconstrictive and hypertensive effects induced by endothelin. An anti-ischemic effect can be noted in particular, the vasoconstrictive effect of endothelin being abolished.

The products of formula (I) are also capable of opposing the stimulating effects of endothelin at the level of all cell types, in particular smooth muscle cells, fibroblasts, neuronal cells and bone cells.

These properties justify their use in therapeutics and a quite particular subject of the invention is as medicaments, the products of formula (I),
said products of formula (I) being in all the possible racemic, enantiomeric and diastereoisomeric isomer forms, as well as the addition salts with pharmaceutically acceptable mineral and organic acids or mineral and organic bases of said products of formula (I).

Therefore a more particular subject of the invention is, as medicaments, the products as defined by formula (I) above, in which:

$R_1$ represents an ethyl, n-propyl, isopropyl, n-butyl, isobutyl or terbutyl radical, A represents a sulphur atom, $R_2$ represents a linear or branched alkyl or alkoxy radical containing at most 4 carbon atoms and substituted by a free, salified or esterified carboxy radical, $R_3$ represents a free, salified or esterified carboxy radical, or a free or salified tetrazolyl radical, Y represents a phenyl radical substituted by a dioxol radical and optionally by a halogen atom, said products of formula (I) being in all the possible racemic or optically-active forms, as well as the addition salts with pharmaceutically acceptable mineral and organic acid or with mineral and organic bases of said products of formula (I).

A quite particular subject of the invention is, as medicaments, the products described hereafter in the examples and notably the products of formula (I) as defined above, the names of which follow:

4-((4-(carboxymethoxy)phenyl)thio)-1-((6-chloro-1,3-benzodioxol-5-yl) methyl)-2-propyl-1H-imidazole-5-carboxylic acid, 4-((4-(2-carboxyethyl)phenyl)thio)-1-((6-chloro-1,3-benzodioxol-5-yl) methyl)-2-(1-methylethyl)-1H-imidadazole-5 -carboxylic acid, 4-((4-carboxyphenyl)thio) 1-((6-chloro 1,3-benzodioxol-5-yl) methyl)-2-propyl-1H-imidazole-5-carboxylic acid, as well as their addition salts with pharmaceutically acceptable mineral or organic acids or with mineral and organic bases.

The medicaments which are a subject of the invention can be used, for example, in the treatment of all vascular spasms, in the treatment of vasospasms following a cerebral haemorrhage, in the treatment of coronary spasms, peripheral vascular spasms as well as in the treatment of renal insufficiency. These medicaments can also be used in the treatment of myocardial infarction, congestive cardiac insufficiency, in the prevention of the post-angioplastic recurrence of stenosis, cardiac and vascular fibroses in the treatment of atherosclerosis, certain forms of hypertension such as in particular pulmonary hypertension, as well as in the treatment of asthma.

The medicaments which are a subject of the invention can also be used in the treatment of osteoporosis, prostatic hyperplasia and as neuronal protectors.

The invention extends to the pharmaceutical compositions containing as active ingredient at least one of the medicaments as defined above.

These pharmaceutical compositions can be administered by buccal or rectal route, by parenteral route or by local route as a topical application on the skin and mucous membranes or by injection by intravenous or intramuscular route.

These compositions can be solid or liquid and can be presented in all the pharmaceutical forms commonly used in human medicine such as, for example, plain or sugar-coated tablets, capsules, granules, suppositories, injectable preparations, ointments, creams, gels and aerosol preparations; they are prepared according to the usual methods. The active ingredient can be incorporated with excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

The usual dose, variable according to the product used, the patient being treated and the illness in question, can be, for example, from 1 to 300 mg per day for an adult, by oral route, or from 1 to 100 mg per day by intravenous route.

Certain starting products of formulae (II) and (XVI) are known and can be prepared for example as indicated in the European Patent EP 168,950.

Other starting products of formulae (II) and (XVI) can in particular be prepared as indicated in the European Patent EP 0,465,368, or also in the examples described hereafter in the experimental part.

Certain starting products of formulae (II) and (XVI) are commercially available, such as for example, the following products of formula (II):

2-propylimidazole, 2-isopropylimidazole, 2-ethylimidazole, 2-methylimidazole.

Examples of commercial products of formula (XVI) are given in Patent EP 0,465,368 or EP 0,503,162.

Certain products of formula (II) can also in particular be prepared from other products of formula (II) for example by subjecting them to one or more of the reactions described above in a) to r), carried out under the conditions also described above.

The starting compounds of formula (VI) such as 2,4,5-tribromoimidazole or also the starting products of formulae (XX) and (XXI) may be commercially available or can be prepared according to the usual methods known to a man skilled in the art.

The starting products of formula (X) are commercially available such as in particular:

methyl chloroformate benzyl chloroformate isobutyl chloroformate ethyl chloroformate N-propyl chloroformate.

The starting products of formulae (VIIIa) and (VIIIb) are commercially available such as in particular:
the following products of formula (VIIIa):

benzaldehyde or butanal the following products of formula (VIIIb):

benzoyl or butyryl chloride.

A preparation process for certain products of formula (III) is also described in the European Patent EP 0,465,368.

Examples of the preparation of compounds of formula (III) are also described in the literature and such examples are given in particular in the U.S. Pat. No. 4,880,804 or for example in the reference Chemistry and Industry Sep. 7 1987 HOWARD and COLQUHOUN pp. 612–617.

In particular, the product of formula (III) which is 6-chloro piperonyl chloride commercially available from ACROS.

Finally a subject of the present invention is, as new industrial products, the compounds of formulae (IV), (V), (IX), (XI) and (XIII), in which, it being understood that in the compounds of formulae (IX) and (XI), W represents the $CH_2$—Y' radical, Y' represents the phenyl radical substituted by a dioxol radical and optionally by a halogen atom or by an alkyl or alkoxy radical containing at most 4 carbon atoms and in which the optional reactive functions are optionally protected by protective groups.

Therefore a particular subject of the invention is the use of the products of formula (I) as defined above, for the preparation of pharmaceutical compositions intended for the treatment of illnesses resulting from an abnormal stimulation of the endothelin receptors and in particular intended for the treatment of hypertension induced by endothelin, all vascular spasms, for the treatment of the after-effects of a cerebral haemorrhage, renal insufficiencies, myocardial infarction, cardiac insufficiency and for the prevention of the recurrence of post-angioplastic stenosis as well as cardiac and vascular fibroses.

The following examples illustrate the invention without however limiting it.

EXAMPLE 1

4-((4-(carboxymethoxy)phenyl)thio)-1-((6-chloro- 1, 3-benzodioxol5-yl)methyl) 2-propyl1H-imidazole5-carboxylic acid STAGE 1: 1-((6-chloro 1,3-benzodioxol-5-yl)methyl)-2-n-propyl1H-imidazole 12 g of 2-n-propyl-1H-imidazole is introduced into 125 ml of anhydrous dimethylformamide, 5.28 g of sodium hydride at 50% in oil is added slowly in fractions, agitation is carried out for 20 minutes then 22.55 g of 6-chloro-piperonyl chloride is added in fractions and agitation is continued for one hour at ambient temperature. The dimethylformamide is evaporated off with a rotary evaporator then the residue is acidified then hydrolyzed using saturated ammonium chloride. Extraction is carried out 3 times with methylene chloride. The organic phase is washed with distilled water, dried, then impasted in ethyl ether and dried.

In this way 22.2 g of expected product (white powder) is obtained.

Control

IR $CHCl_3$ $cm^{-1}$

Absence of N—H

Heterocycle and aromatic: 1627, 1575, 1523, 1506, 1483.

STAGE 2: 1-((6-chloro-1,3-benzodioxol5-yl)-methyl)-4,5-dibromo-2-n-propyl-1H-imidazole 25 g of the product obtained in Stage 1 above is introduced into 150 ml of anhydrous methylene chloride, 35.2 g of N-bromo succinimide is added in fractions and the reaction mixture is taken to reflux of the methylene chloride for 2 hours. The solution is washed with 1M soda then the organic phase is washed with distilled water then with saturated sodium chloride. The organic phase is dried, filtered, concentrated, impasted in ethyl ether and dried. In this way 34.87 g of expected product (yellow powder) is obtained.

Control

IR $CHCl_3$ $cm^{-1}$

Heterocycle and aromatic: 1627, 1506, 1484.

STAGE 3: 1-((6-chloro-1,3-benzodioxol-5-yl) methyl)-4-bromo 2-n-propyl-1H-imidazole-5-carboxaldehyde 20 g of the product obtained in Stage 2 above is introduced into 100 ml of anhydrous tetrahydrofuran. 30.6 ml of a 3M solution of ethyl magnesium bromide in diethyl ether is added, agitation is carried out for 20 minutes at ambient temperature then 35.6 ml of dimethyl-formamide is introduced and agitation is continued for 2 hours. The solution is acidified, hydrolyzed with saturated ammonium chloride, then extracted with ethyl acetate. The organic phase is washed with distilled water then with saturated sodium chloride. The organic phase is dried, filtered and concentrated. Purification is carried out by chromatography on silica with ethyl acetate 2-cyclohexane 8 as eluant, and drying. In this way 13.11 g of expected product (white powder) is obtained.

Control

IR $CHCl_3$ $cm^{-1}$

Carbonyl: 1669

Heterocycle and aromatic: 1506, 1485.

STAGE 4: 1-((6-chloro-1,3-benzodioxol 5-yl) methyl)-4-((4-hydroxyphenyl)thio)-2-n-propyl1H-imidazole-5-carboxaldehyde 1.8 g of hydroxythiophenol, as well as 12 ml of anhydrous tetrahydrofuran and 1.76 g of sodium hydride in small fractions are mixed together. After 15 minutes of agitation at ambient temperature, 58 ml of anhydrous dimethylformamide and 1.8 g of the product obtained in Stage 3 above are added. The mixture is agitated for one hour at ambient temperature, then hydrolyzed and acidified using sodium chloride. The aqueous phase is extracted twice with 75 ml of ethyl acetate. The combined organic phases are washed with water, then with a saturated solution of sodium chloride. After drying, filtering, concentrating, and impasting in ethyl ether, 1.72 g of expected product (cream-coloured solid) is obtained. M.p. 241.5° C.

Control

IR Nujol $cm^{-1}$

Absorption OH/NH

>=0~1660

Heterocycle and aromatic: 1594, 1576, 1499, 1484.

STAGE 5: 1-((6-chloro-1,3-benzodioxol-5-yl) methyl)-4-((4-(ethoxycarbonylmethoxy)phenyl)thio)-2-n-propyl1H-imidazole5-carboxaldehyde 5 0.7 g of the product obtained in Stage 4 above, 18 ml of tetrahydrofuran, 9 ml of dimethylformamide and 153 mg of sodium hydride in small fractions are mixed together. After 10 minutes of agitation at ambient temperature, 0.21 ml of ethyl bromoacetate is added and agitation is maintained at ambient temperature. 35 ml of water is added, then the aqueous phase is extracted with ethyl acetate. The combined organic phases are washed with water, then with a saturated solution of sodium chloride. After drying, filtration and concentration, the residue is chromatographed on silica, with 90% methylene chloride, 10% ethyl acetate as eluant.

In this way 0.78 g of expected product (slightly yellow oil) is obtained.

Control

IR $CHCl_3$ $cm^{-1}$

Absence of OH

>=0: 1756, 1734, 1663

Heterocycle and aromatic: 1593, 1575, 1505, 1493, 1484.

STAGE 6: ethyl 1-((6-chloro-1,3-benzodioxol-5-yl)methyl)-2-n-propyl-1H-imidazole-5-cyano-4-((4-methoxyphenylthio)carboxylate 15 ml of isopropanol is saturated with ammonia gas. The product obtained in Stage 5 above is dissolved in 10 ml of isopropanol, 1.98 g of manganese oxide is added, the reaction medium is heated in a water-bath for about 15 minutes then agitated for approximately one night at ambient temperature. After filtration and concentration, the residue is purified by chromatography on silica, with 95% methylene chloride, 5% methanol as eluant.

In this way 400 mg of expected product is obtained.

STAGE 7: 4-((4-(carboxymethoxy)phenyl)thio)-1-((6-chloro-1,3-benzodioxol-5-yl)methyl)-2-propyl-1H-imidazole-5-carboxylic acid 400 mg of the product obtained in Stage 6 above is introduced into 25 ml of ethanol, 10 ml of soda (5N) is added and the reaction mixture is taken to reflux overnight.

The ethanol is evaporated off, and the remaining product is taken to reflux in 10 ml of SN soda, for 4 hours. Then 20 ml of distilled water s added, followed by filtration, 35 ml of 2N hydrochloric acid is added and the precipitate obtained is separated off, washed abundantly with distilled water, then impasted in ethanol. Recrystallization is carried out from an ethanol, ethyl acetate, methylene chloride mixture (50%, 25%, 25%) and in this way 125 mg of expected product is obtained. M.p. =202° C.

Control

IR Nujol cm$^{-1}$

General absorption OH/NH region

C=O: 1735, 1660

Heterocycle and aromatic: 1593, 1576, 1502, 1493, 1485.

EXAMPLE 2

4-((4-(2-carboxyethyl)phenyl)thio)-1-((6-chloro-1,3-benzodioxol-5-yl)methyl)-2-(1-methylethyl)-1H-imidazole-5-carboxaldehyde STAGE 1: 1-((6-chloro-1,3-benzodioxol-5-yl) methyl)-2-isopropyl-1H-imidazole The operation is carried out as in Stage 1 of Example 1, using 22 g of 2-isopropyl 1H-imidazole instead of 2-propyl-1H-imidazole. In this way 27.8 g of expected product is obtained.

STAGE 2: 1-((6-chloro-1,3-benzodioxol-5-yl)methyl)-4,5-dibromo-2-isopropyl-1H-imidazole The operation is carried out as in Stage 2 of Example 1, using 27.8 g of the product obtained in Stage 1 above instead of the product obtained in Stage 1 of Example 1. In this way 39.2 g of expected product is obtained.

STAGE 3: 1-((6-chloro 1,3-benzodioxol-5-yl)methyl)-4-bromo 2-isopropyl-1H-imidazole-5-carboxaldehyde The operation is carried out as in Stage 3 of Example 1, using 25 g of the product obtained in Stage 2 above, instead of the product obtained in Stage 2 of Example 1.

In this way 11.8 g of expected product is obtained.

STAGE 4: 4-((4-(2-carboxyethyl)phenyl)thio) 1-((6-chloro 1,3-benzodioxol 5-yl)methyl) 2-(1-methylethyl) 1H-imidazole 5-carboxaldehyde The operation is carried out as in Stage 4 of Example 1, starting with 770 mg of the product obtained in Stage 3 above, instead of the product obtained in Stage 3 of Example 1 and 550 mg of N3 in order to obtain 610 mg of expected product (amorphous solid).

EXAMPLE 3

4-((4-(2-carboxyethyl)phenyl)thio)-1-((6-chloro-1,3-benzodioxol-5-yl) methyl)-2-(1-methylethyl)-1H-imidazole-5-carboxylic acid STAGE 1: 3-[4-[[1-[(6-chloro-1,3-benzodioxol-5-yl)methyl)-5-cyano-2-(1-methylethyl)-1H-imidazol-4-yl]thio]-phenoxy]-propanoic acid The operation is carried out as in Stage 6 of Example 1 starting with 600 mg of the product of Example 2, and in this way 200 mg of expected product is obtained.

STAGE 2: 4-((4-(2-carboxyethyl)phenyl)thio)-1-((6-chloro-1,3-benzodioxol 5-yl) methyl)-2-(1-methylethyl)-1H-imidazole-5-carboxylic acid The operation is carried out as in Stage 7 of Example 1 starting with 200 mg of the product obtained in Stage 1 above and in this way 115 mg of expected product is obtained. M.p.=198° C.

EXAMPLE 4

4-((4-carboxymethyl) 2,3,5,6-tetrafluorophenyl)thio) 1-((6-chloro 1,3-benzodioxol-5-yl)methyl) 2-propyl 1H-imidazole 5-carboxylic acid STAGE 1: ethyl cyano-[(1-oxobutyl) amino]acetate 5 g of ethyl (hydroxyimino) cyanoacetate, 40 cm$^3$ of tetrahydrofuran, 11.5 cm$^3$ of butyric anhydride and 2.5 g of platinum are mixed together and the mixture is agitated under a hydrogen atmosphere until saturation is obtained. After filtration, rinsing with 5×15 cm$^3$ of ethyl ether, and evaporating off the ether, 200 cm$^3$ of essence G is added little by little, followed by separation, washing with 3×10 cm$^3$ of essence G and drying at about 75° C. After concentration to −10 cm$^3$, 50 cm$^3$ of essence G is added, the medium is left to crystallize for 30 minutes at ambient temperature, followed by separation, washing with 3×3 cm$^3$ of essence G and drying at approximately 75° C. 5.73 g of product is obtained. M.p. =110° C.

Recrystallization for analyses:

540 mg of the product obtained is dissolved in 50 cm$^3$ of isopropyl ether under reflux, the solution is filtered, concentration is carried out, the resultant product is left at rest for about one hour at ambient temperature, followed by separation, washing with isopropyl ether and drying. 440 mg of expected product is obtained. M.p. =110° C.

STAGE 2: ethyl 3-amino 2-[(1-oxobutyl)amino]3-(methylthio) 2-propenoate 1.4 ml of triethylamine is added to a solution of 20 g of nitrile obtained in Stage A above, in 400 ml of ethanol, the reaction medium is cooled down to about −10° C. and about 22 g of methylmercaptan is introduced by bubbling it through. Agitation is carried out for about 72 hours at 0° C. The excess methanethiol is eliminated, the ethanol is driven off, the residue is impasted in essence G, followed by filtration and drying. 24.3 g of expected product (colourless crystals) is obtained.

M.p.$_{K115}$=120–124° C.

STAGE 3: ethyl 4-(methylthio) 2-propyl 1H-imidazole 5-carboxylate

A solution of 12.9 g of 4-dimethylaminopyridine in 90 cm$^3$ of methylene chloride is added to 20.1 g of phosphorus pentachloride in 300 cm$^3$ of methylene chloride, cooled down to about −70° C. The reaction medium is maintained at about −70° C. for about another 15 minutes then a solution of 12 g of the product obtained in Stage B above in 120 cm$^3$ of methylene chloride is introduced. The mixture is allowed to return to ambient temperature and maintained under agitation for about 22 hours. The reaction mixture is poured into 2.5 liters of water+ice and neutralized by the addition of about 60 g of sodium bicarbonate. Agitation is carried out for about another 30 minutes, followed by decanting and extraction with 500 cm$^3$ of methylene chloride. The extracts are washed with salt water, dried and the solvent is driven off at about 50° C. Purification is carried out by chromatography on silica with methylene chloride—ethyl acetate (90-10) then methylene chloride—ethyl acetate (80-20) as eluant. The solvents are driven off at about 50° C., followed by impasting in essence G, filtration and drying. 7.4 g of expected product (colourless crystals) is obtained. M.P.$_{K95}$=85° C.

STAGE 4: ethyl 1-[(6-chloro-1,3-benzodioxol-5-yl) methyl]-4-(methylthio)-2-propyl-1H-imidazole-5-carboxylate 10 g of the product obtained in Stage 3 above and 13.5 g of 6-chloro piperonyl chloride are introduced into 100 ml of dimethylformamide, 9 g of potassium carbonate is added and the whole is heated to 100° C. for one hour. After cooling down to ambient temperature, the reaction medium is poured over ice, the precipitate obtained is filtered out then it is impasted in isopropyl ether. In this way 9.25 g of expected product is obtained.

STAGE 5: ethyl 1-[(6-chloro-1,3-benzodioxol-5-yl)methyl]-4-(methylsulphinyl)-2-propyl-1H-imidazole-5-carboxylate 9.26 g of the product obtained in Stage 4 above is introduced into 400 ml of methylene chloride at 0° C. and 5.8 g of metachloroperbenzoic acid is added. Agitation is carried out for one hour at ambient temperature and the reaction medium is washed with sodium and potassium hydride, extraction is carried out with methylene chloride, the extracts are washed with water, dried, and the solvent is evaporated off. After chromatography, 8.8 g of expected product is obtained. M.p.=187° C.

STAGE 6: ethyl 1-[(6-chloro-1,3-benzodioxol-5-yl)methyl]-4-mercapto-2-propyl-1H-imidazole-5-carboxylate 800 mg of the product obtained in Stage 5 above is introduced into 16 ml of methylene chloride and 0.54 ml of trifluoroacetic anhydride is added. Agitation is carried out for 30 minutes, followed by evaporation to dryness and the residue is taken up in 10 ml of methanol and 4 ml of triethylamine. After agitation for 30 minutes, extraction is carried out with chloroform, the extracts are washed with a saturated solution of ammonium chloride, dried and evaporated to dryness. In this way 720 mg of expected product is obtained.

STAGE 7: ethyl 1-[(6-chloro-1,3-benzodioxol-5-yl) methyl]-4-[[(4-carboxymethyl) 2,3,5,6-tetrafluorophenyl] thio) 2-propyl 1H-imidazole 5-carboxylate 1 g of the product obtained in Stage 6 above is introduced into 50 ml of tetrahydrofuran, 130 mg of a suspension of sodium hydride at 60% in oil is added and the whole is left under agitation for 15 minutes at ambient temperature. Then 830 mg of methyl pentafluorophenyl acetate in solution in 20 ml of dimethylformamide is added, and the reaction medium is left under agitation for 15 hours at ambient temperature. It is hydrolyzed by the addition of dilute hydrochloric acid and extraction is carried out: with ethyl acetate. In this way, after chromatography on silica (eluant: cyclohexane-AcOEt 80-20), 900 mg of expected product is obtained.

STAGE 8: 4-((4-carboxymethyl) 2,3,5,6-tetrafluorophenyl) thio) 1-((6-chloro 1,3-benzodioxol-5-yl)methyl) 2-propyl 1H-imidazole 5-carboxylic acid 900 mg of the product obtained in Stage 7 in 50 mL of ethanol is agitated for 72 hours in the presence of 20 ml of 2N soda. The solvent is evaporated off under reduced pressure, the residue is taken up in water, followed by filtration and acidification by the addition of N hydrochloric acid, the precipitate is separated out, washed with water, dried at 500C under reduced pressure, purified by impasting in isopropyl ether and 680 mg of expected product is collected. M.p.=132° C.

By operating as in Stages 4 to 7 of Example 1 starting with the compound obtained in Stage 3 and replacing the hydroxythiophenol with methyl 4-thiobenzoate (J. Org. Chem. 1975, 40 (12) 1745–1748), the following product was prepared:

EXAMPLE 5

4-((4-carboxyphenyl)thio) 1-((6-chloro 1,3-benzodioxol-5-yl)methyl) 2-propyl 1,3-imidazole 5-carboxylic acid M.p.=210° C.

EXAMPLE 6

PHARMACEUTICAL COMPOSITION

Tablets were prepared corresponding to the following formula:

| | |
|---|---|
| Product of Example 1 | 50 mg |
| Excipient for a tablet made up to | 200 mg |

(detail of the excipient: lactose, talc, starch, magnesium stearate).

Pharmacological Results

1) Study of the Affinity for the Endothelin A Receptor

A membrane preparation is prepared from the heart (ventricles) of a rat. The tissue is ground up in a POLYTRON in a 50 mM Tris buffer pH=7.4.

After 30 minutes at 25° C. (W.B.) the homogenate is centrifuged at 30,000 g for 15 minutes (2 centrifugations with intermediate take-up in the Tris buffer pH. 7.4).

The pellets are suspended in an incubation buffer (25 mM Tris, 5 microg/ml pepstatin A, 3 microg/ml aprotinin, 0.1 mM PMSF, 3 mM EDTA, 1 mM EGTA pH 7.4).

2 ml aliquoted fractions are distributed in hemolysis tubes and $^{125}$I endothelin (approximately 50,000 dpm/tube) and the product to be studied are added. (The product is first tested at 3×10$^{-5}$ M three times). When the tested product displaces more than 50% of radioactivity specifically bound to the receptor, it is tested again according to a range of 7 concentrations in order to determine the concentration which inhibits by 50% the radioactivity specifically bound to the receptor. In this way the 50% inhibitory concentration is determined.

The non-specific bond is determined by the addition of endothelin at 10$^{-6}$ M (three times). After incubation at 25° C. for 60 minutes, replacing in a water-bath at 0° C. for 5 minutes, filtration under reduced pressure and rinsing with Tris buffer pH 7.4, the radioactivity is counted in the presence of scintillating Triton.

The result is expressed directly as the 50% inhibitory concentration (IC50), that is to say the concentration of product studied, expressed in nM, necessary to displace 50% of the specific radioactivity fixed to the receptor studied.

Result

The IC$_{50}$'s found for the products of the examples are given in Table I hereafter, in nanomoles.

TABLE I

| Product of examples | Endothelin A receptor IC$_{50}$ in nanomoles |
| --- | --- |
| 1 | 2,5 |
| 3 | 2,5 |

2) Study of the Affinity for the Endothelin B Receptor

A membrane preparation is prepared from the rear cortex plus the cerebellum of a rat. The tissue is ground up in a POLYTRON in a 50 mM Tris buffer pH=7.4.

After 30 minutes at 250C (W.B.) the homogenate is centrifuged at 30,000 g for 15 minutes (2 centrifugations with intermediate take-up in the Tris buffer pH. 7.4).

The pellets are suspended in an incubation buffer (25 mM Tris, 5 microg/ml pepstatin A, 3 microg/ml aprotinin, 0.1 mM PMSF, 3mM EDTA, 1 mM EGTA pH 7.4).

2 ml aliquoted fractions are distributed in hemolysis tubes and 125I endothelin (approximately 50,000 dpm/tube) and the product to be studied are added. (The product is first tested at $3 \times 10^{-5}$ M three times). When the tested product displaces more than 50% of the radioactivity specifically bound to the receptor, it is tested again according to a range of 7 concentrations in order to determine the concentration which inhibits by 50% the radioactivity specifically bound to the receptor. In this way the 50% inhibitory concentration is determined.

The non-specific bond is determined by the addition of endothelin at $10^{-6}$ M (three times). After incubation at 25° C. for 60 minutes, replacing in a water-bath at 0° C. for 5 minutes, filtration under reduced pressure and rinsing with Tris buffer pH 7.4, the radioactivity is counted in the presence of scintillating Triton.

The result is expressed directly as the 50% inhibitory concentration (IC$_{50}$), that is to say as the concentration of product studied, expressed in nM, necessary to displace 50% of the specific radioactivity fixed to the receptor studied.

The IC$_{50}$'s found for the products of the examples are given in Table I hereafter, in nanomoles.

Results

TABLE I

| Product of examples | Endothelin B receptor IC$_{50}$ in nanomoles |
| --- | --- |
| 1 | 88,5 |
| 3 | 78,4 |

3) Test for Antagonistic Activity of Endothelin in a Demedullated Rat

Male Sprague-Dawley rats (250 to 350 g) are anaesthetized (sodium pentobarbital 60 mg/kg injected by intraperitoneal route). The animal is placed under assisted respiration and a bilateral section of the vagus nerves is carried out. The rat is then demedullated.

The average arterial pressure is recorded with a heparin catheter (PE50) introduced into the carotid of the animal and connected via a pressure sensor and an amplifier to a recorder (Gould pressure processor). A catheter is implanted in the pudendal vein in order to allow injection of the molecules to be studied. After a stabilization period (about 15 minutes), the product or the solvent is injected 10 minutes before a range of increasing doses of endothelin which are injected every 2 minutes (0.1–0.3–1–3–10 ug/kg).

The antagonistic activity of the products is estimated by the percentage inhibition of the increase in pressure induced by endothelin at doses of 3 and 10 ug/kg.

Results

| | | % inhibition of vasoconstriction | |
| --- | --- | --- | --- |
| EXAMPLES | Doses mg/kg | Et$_1$ 3 µg/kg | Et$_1$ 10 µg/kg |
| 1 | 10 | −52 | −50 |
| 3 | 10 | +7 | −31 |

We claim:

1. A compound selected from the group consisting of a compound of the formula

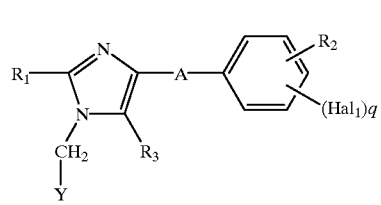

I in which

R$_1$ is alkyl of 2 to 6 carbon atoms,

A is sulphur or oxygen,

R$_2$ is selected from the group consisting of free carboxy, salified carboxy or carboxy esterified with an alkanol of 1 to 6 carbon atoms, free or salified tetrazolyl and alkyl, alkoxy and alkylthio of 1 to 4 carbon atoms and substituted by a free carboxy, salified carboxy or carboxy esterified with an alkanol of 1 to 6 carbon atoms or free or salified tetrazolyl, Hal$_1$ is halogen and q is an integer from 0 to 4, R$_3$ is selected from the group consisting of formyl, a free carboxy, salified carboxy or carboxy esterified with an alkanol of 1 to 6 carbon atoms and free or salified teterazolyl, Y is phenyl substituted by dioxol and optionally by a halogen, or by an alkyl or alkoxy of 1 to 4 carbon atoms, said products of formula I being in all possible racemic, enantiomeric and diastereoisomeric isomer forms, and their non-toxic, pharmaceutically acceptable addition salts with acids and bases.

2. A compound of claim 1 in which:

R$_1$ is selected from the group consisting of ethyl, n-propyl, isopropyl, n-butyl, isobutyl and terbutyl, A is sulfur, R$_2$ is alkyl or alkoxy of 1 to 4 carbon atoms and substituted by a free carboxy, salified carboxy, carboxy esterified with an alkanol of 1 to 6 carbon atoms, R$_3$ is selected from the group consisting of free carboxy, salified carboxy, esterified with an alkanol of 1 to 6 carbon atoms and a free or salified tetrazolyl, Y is phenyl substituted by a dioxol and unsubstituted or substituted by a halogen.

3. A compound of claim 1 selected from the group consisting of 4-((4-(carboxymethoxy)phenyl)thio) 1-((6-chloro-1,3-benzodioxol-5-yl)methyl) 2-(1-methylethyl)-1H-imidazole-5-carboxylic acids and 4-((4-carboxyphenyl)thio) 1-((6-chloro 1,3-benzodioxol-5-yl)methyl) 2-propyl 1H-imidazole 5-carboxylic acid.

4. A composition for reducing abnormal stimulation of the endothelin receptors comprising an amount of a compound of claim 1 sufficient to reduce abnormal stimulation of the endothelin receptors and a pharmaceutical carrier.

5. A method of reducing abnormal stimulation of the endothelin receptors in warm-blooded animals comprising administering to warm-blooded animals in need thereof an effective amount of a compound of claim 1 sufficient to reduce the abnormal stimulation of the endothelin receptors.

* * * * *